(12) United States Patent
Gaynor-Krupnick

(10) Patent No.: US 8,784,906 B2
(45) Date of Patent: Jul. 22, 2014

(54) ORGANIC LUBRICANT

(76) Inventor: Darlene Gaynor-Krupnick, Great Falls, VA (US)

( * ) Notice: Subject to any disclaimer, the term of this patent is extended or adjusted under 35 U.S.C. 154(b) by 0 days.

(21) Appl. No.: 13/448,246

(22) Filed: Apr. 16, 2012

(65) Prior Publication Data

US 2013/0071485 A1    Mar. 21, 2013

Related U.S. Application Data

(60) Provisional application No. 61/475,621, filed on Apr. 14, 2011.

(51) Int. Cl.
*A61K 36/00* (2006.01)
*A61K 36/30* (2006.01)
*A61K 36/28* (2006.01)

(52) U.S. Cl.
USPC .......................... 424/725; 424/744; 424/764

(58) Field of Classification Search
USPC ......................... 424/764, 725, 744
See application file for complete search history.

(56) References Cited

U.S. PATENT DOCUMENTS 7,205,012 B1 *   4/2007   Hill ............................. 424/764
2011/0171156 A1 *   7/2011   Chrysopoulo et al. ..... 424/78.02

FOREIGN PATENT DOCUMENTS

DE     102005003708    *   8/2006

OTHER PUBLICATIONS

Burlando et al. Herbal Principals in Cosmetics; Properties and Mechanisms of Action; CRC Press, Boca Raton, FL; 2010, pp. 29-40.*

* cited by examiner

*Primary Examiner* — Patricia Leith
(74) *Attorney, Agent, or Firm* — Mark A. Catan; Miles & Stockbridge P.C.

(57) ABSTRACT

A vaginal lubricant of primarily organic materials has excellent properties for relieving vaginal dryness.

1 Claim, 3 Drawing Sheets

INGREDIENT LIST

Percent Organic: 95%

| Ingredient | Category | Allowance | Organic % | % of formulation | % salt | % water | saltwater | Calculated Cells Nonorganic | Organic |
|---|---|---|---|---|---|---|---|---|---|
| JOJOBA OIL odorless | Organic | Organic | 95.00% | 10 | | | | 0.5 | 9.5 |
| sunflower oil | Organic | Organic | 95.00% | 77.87799 | 0.00% | 0.00% | | 3.893995 | 73.984005 |
| beeswax (cera alba) | Organic | Organic | 95.00% | 11 | | | | 0.55 | 10.45 |
| cocoa butter | Organic | Organic | 95.00% | 1 | | | | 0.05 | 0.95 |
| shea butter | Organic | Organic | 95.00% | 0.01 | | | | 0.0005 | 0.0095 |
| evening primrose oil | Organic | Organic | 95.00% | 0.001 | | | | 0.00005 | 0.00095 |
| aloe | Organic | Organic | 95.00% | 0.01 | | | | 0.0005 | 0.0095 |
| borage oil | Organic | Organic | 95.00% | 0.001 | | | | 0.00005 | 0.00095 |
| flax seed oil(flaxseed) | Organic | Organic | 95.00% | 0.1 | | | | 0.005 | 0.095 |
| extract blend of (arnica, comfrey/symphatic) | Organic | Organic | 95.00% | 0.00001 | | | | 0.0000005 | 0.0000095 |
| coconut oil | Organic | Organic | 95.00% | 0.00001 | | | | 0.0000005 | 0.0000095 |
| Totals: | | | | 100.00000 | | | | 5.00001 | 95.00009 |

Fig. 3

ORGANIC LUBRICANT

CROSS REFERENCE TO RELATED APPLICATIONS

This application claims the benefit of U.S. Provisional Application 61/475,621, filed Apr. 14, 2011.

BACKGROUND

Vaginal dryness is a common concern for which remedies are known, including vaginal lubricants. Dryness is a common following menopause in women and also after childbirth and may result from diseases and/or treatments thereof. Vaginal dryness can negatively impact the psychological and physical health of women.

In recent years, consumers have become increasingly concerned about the safety of synthetic materials that are consumed or used on the body. There is a growing movement toward organic materials in products such as shampoo. At present, there is a need for organic vaginal lubricants and particularly lubricants with high performance.

SUMMARY

A vaginal lubricant of primarily organic materials has excellent properties for relieving vaginal dryness.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 3 defines the composition tested.

DETAILED DESCRIPTION OF THE EMBODIMENTS

Figure 1:
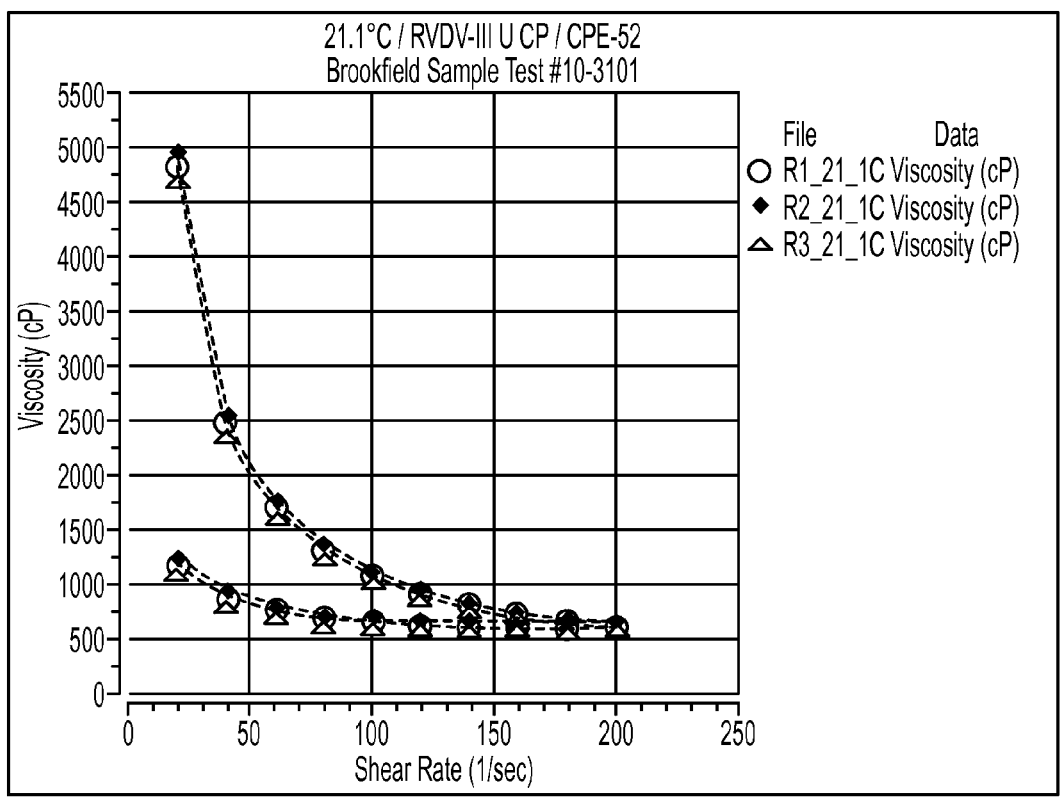
FIG. 1 shows viscosity versus shear rate of a sample of the composition defined in FIG. 3 at 21 C, where the speed of the viscosimeter was first reduced and then increased so that the viscosity is shown to change after being sheared.
Figure 2:
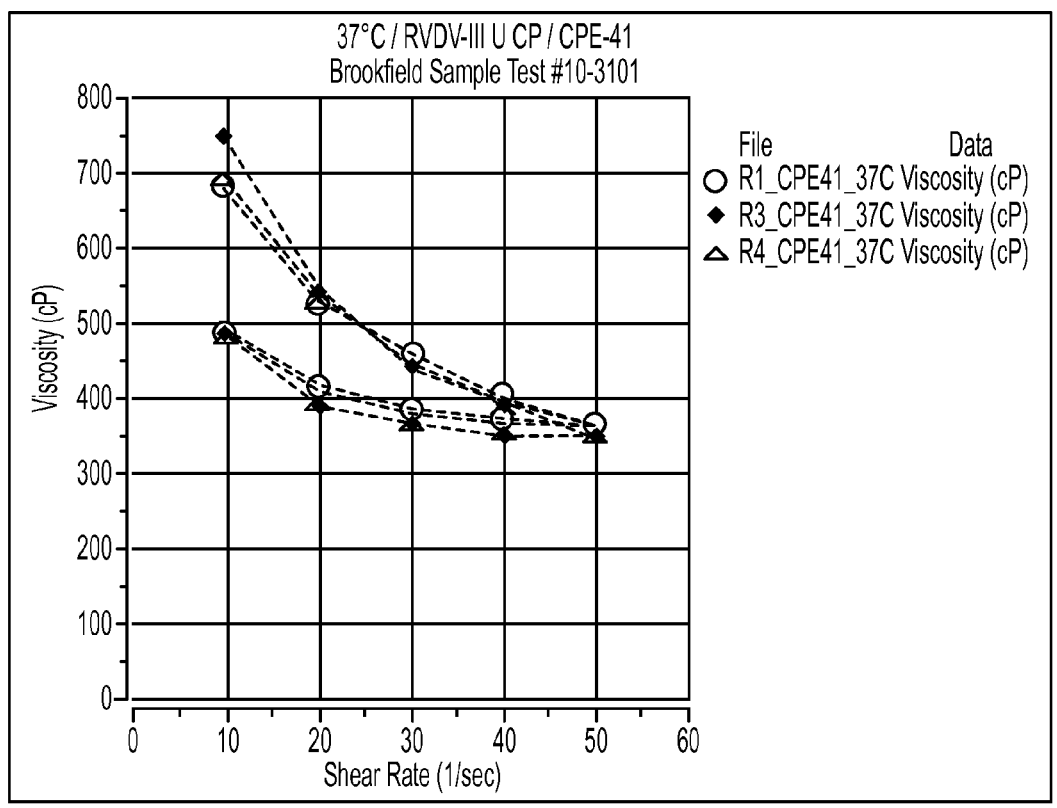
FIG. 2 shows viscosity versus shear rate of a sample of the composition defined in FIG. 3 at 37 C, where the speed of the viscosimeter was first reduced and then increased so that the viscosity is shown to change after being sheared.

An embodiment of the disclosed subject matter can include a vaginal lubricant comprising a base material which may be a non-synthetic oil selected from *Cera Alba* (beeswax) and sunflower oil, and which further can include Shea Butter, Cocoa seed extract, Evening Primrose, Borago seed oil, Lavender Flower extract, and *Aloe Vera* in such combination as to provide a shear thinning effect.

Another embodiment of the disclosed subject matter can include a vaginal lubricant comprising: a combination of ingredients effective to provide a viscosity below 2000 cP at a shear rate of 100 inverse seconds at a temperature of at least 21° C., wherein the combination of ingredients comprises: 10% jojoba oil, 77.88% sunflower oil, 11% beeswax, 1% cocoa butter, 0.01% shea butter, 0.001% evening primrose oil, 0.01% aloe, 0.001% borage oil, 0.1% flax seed oil, 0.00001% extract blend of arnica and comfrey and 0.00001% coconut oil.

Various strain forces were applied to the above compound to determine its properties. A change was appreciated in texture from a solid to a liquid with applied shear forces with and without changes in temperature as well. The compound, consequently, with the applied ratios as seen in the following provides the property changes described.

As shear rate increases 1/sec at body temperature of 37 degrees Celcius, viscosity measured in cP decreased from approximately 700 cP to 350 cP (see graft). At room temperature (21.1 degrees Celcius), viscosity changed from 2500 to 500 cP with speed rate forces in RPM and shear rate as well. Change in viscosity was appreciated with change in temperature, change in shear stress and shear rate unlike other vaginal moisturizers on the market.

Attached graphs and data listings show the results of testing. Conditions were selected so that all measurements were between 10 and 100% of full scale range. A Brookfield RVDV-III Ultra CP Rheometer was used; a CPE-52 cone spindle was used for tests at 21° C., and a CPE-41 cone spindle was used for the test at 37° C. Sample temperatures were maintained by using a Brookfield TC-502 P Programmable Temperature Bath connected to the sample cup. The compound was thixotropic and the viscosities measured at various shear rates were lower at the higher temperature. The larger CPE-41 cone spindle was used at 37° C., to ensure sufficient sensitivity when measuring the lower viscosities.

In addition, the present compound, no bacterial changes were appreciated in microbiologic testing by Micro Quality Labs, Inc. at 1 month of testing with a challenge test and at 1.5 years later as well. Certificate of Analysis was received indicating no growth with Enrichment testing, <10 cfu/gm for TPC and <10 cfu/gm for yeast and mold.

The compound is expected to improve vaginal tissue quality and decrease the incidence of dyspareunia without the concerns and contraindications of hormones. The ingredient composition along with the viscosity findings are unique to the product in this category of vaginal lubricants and moisturizers.

The foregoing descriptions apply, in some cases, to examples generated in a laboratory, but these examples can be extended to production techniques. For example, where quantities and techniques apply to the laboratory examples, they should not be understood as limiting.

The following tables present the test data used to create the figures and present other related data.

TABLE 1

| | | | | | | | | |
|---|---|---|---|---|---|---|---|---|
| | | | | First run for 21 C. sample. | | | | |
| # | Viscosity (cP) | Speed (RPM) | % Torque (%) | Shear Stress (D/cm²) | Shear Rate (1/sec) | Temperature (° C.) | Bath (° C.) | Time Interval (mm:ss.t) |
| 1 | 4822.09 | 10.00 | 48.6 | 964.42 | 20.00 | 20.9 | EEEE | 00:00:31.6 |
| 2 | 2490.42 | 20.00 | 50.2 | 996.17 | 40.00 | 20.9 | EEEE | 00:00:30.2 |
| 3 | 1706.58 | 30.0 | 51.6 | 1023.95 | 60.00 | 20.9 | EEEE | 00:00:30.2 |
| 4 | 1529.55 | 40.00 | 53.6 | 1063.64 | 80.00 | 20.9 | EEEE | 00:00:30.2 |
| 5 | 1107.30 | 50.00 | 55.8 | 1107.30 | 100.00 | 20.9 | EEEE | 00:00:30.3 |

TABLE 1-continued

First run for 21 C. sample.

| # | Viscosity (cP) | Speed (RPM) | % Torque (%) | Shear Stress (D/cm$^2$) | Shear Rate (1/sec) | Temperature (° C.) | Bath (° C.) | Time Interval (mm:ss.t) |
|---|---|---|---|---|---|---|---|---|
| 6 | 945.90 | 60.00 | 57.2 | 1135.08 | 120.00 | 20.9 | EEEE | 00:00:30.3 |
| 7 | 843.37 | 70.00 | 59.5 | 1180.72 | 140.00 | 20.9 | EEEE | 00:00:30.3 |
| 8 | 761.51 | 80.00 | 61.4 | 1218.42 | 160.00 | 20.9 | EEEE | 00:00:30.2 |
| 9 | 700.05 | 90.00 | 63.5 | 1260.09 | 180.00 | 20.9 | EEEE | 00:00:30.2 |
| 10 | 649.89 | 100.00 | 65.5 | 1299.78 | 200.00 | 20.9 | EEEE | 00:00:30.3 |
| 11 | 639.42 | 90.00 | 58.0 | 1150.95 | 180.00 | 20.9 | EEEE | 00:00:30.2 |
| 12 | 641.21 | 80.00 | 51.7 | 1025.93 | 160.00 | 20.9 | EEEE | 00:00:30.2 |
| 13 | 647.76 | 70.00 | 45.7 | 906.87 | 140.00 | 20.9 | EEEE | 00:00:30.2 |
| 14 | 661.47 | 60.00 | 40.0 | 793.76 | 120.00 | 20.9 | EEEE | 00:00:30.3 |
| 15 | 688.59 | 50.00 | 34.7 | 688.59 | 100.00 | 20.9 | EEEE | 00:00:30.2 |
| 16 | 721.83 | 40.00 | 29.1 | 577.46 | 80.00 | 20.9 | EEEE | 00:00:30.3 |
| 17 | 787.15 | 30.00 | 23.8 | 472.29 | 60.00 | 20.9 | EEEE | 00:00:30.2 |
| 18 | 883.06 | 20.00 | 17.8 | 353.22 | 40.00 | 20.9 | EEEE | 00:00:30.2 |
| 19 | 1190.64 | 10.00 | 12.0 | 238.13 | 20.00 | 20.9 | EEEE | 00:00:30.2 |

TABLE 2

Second run for 21 C. sample.

| # | Viscosity (cP) | Speed (RPM) | % Torque (%) | Shear Stress (D/cm$^2$) | Shear Rate (1/sec) | Temperature (° C.) | Bath (° C.) | Time Interval (mm:ss.t) |
|---|---|---|---|---|---|---|---|---|
| 1 | 4980.84 | 10.00 | 50.2 | 996.17 | 20.00 | 20.9 | EEEE | 00:00:31.5 |
| 2 | 2574.76 | 20.00 | 51.9 | 1029.90 | 40.00 | 20.9 | EEEE | 00:00:30.2 |
| 3 | 1776.04 | 30.0 | 53.7 | 1065.62 | 60.00 | 20.9 | EEEE | 00:00:30.3 |
| 4 | 1399.00 | 40.00 | 56.4 | 1119.20 | 80.00 | 20.9 | EEEE | 00:00:30.2 |
| 5 | 1158.89 | 50.00 | 58.4 | 1158.89 | 100.00 | 20.9 | EEEE | 00:00:30.3 |
| 6 | 1003.78 | 60.00 | 60.7 | 1204.53 | 120.00 | 20.9 | EEEE | 00:00:30.2 |
| 7 | 881.64 | 70.00 | 62.2 | 1234.30 | 140.00 | 20.9 | EEEE | 00:00:30.2 |
| 8 | 803.68 | 80.00 | 64.8 | 1285.89 | 160.00 | 20.9 | EEEE | 00:00:30.3 |
| 9 | 743.05 | 90.00 | 67.4 | 1337.49 | 180.00 | 20.9 | EEEE | 00:00:30.2 |
| 10 | 681.64 | 100.00 | 68.7 | 1363.28 | 200.00 | 20.9 | EEEE | 00:00:30.2 |
| 11 | 674.70 | 90.00 | 61.2 | 1214.45 | 180.00 | 20.9 | EEEE | 00:00:30.2 |
| 12 | 677.18 | 80.00 | 54.6 | 1083.48 | 160.00 | 20.9 | EEEE | 00:00:30.3 |
| 13 | 687.45 | 70.00 | 48.5 | 962.43 | 140.00 | 20.9 | EEEE | 00:00:30.2 |
| 14 | 701.15 | 60.00 | 42.4 | 841.39 | 120.00 | 20.9 | EEEE | 00:00:30.2 |
| 15 | 720.34 | 50.00 | 36.3 | 720.34 | 100.00 | 20.9 | EEEE | 00:00:30.3 |
| 16 | 759.03 | 40.00 | 30.6 | 607.23 | 80.00 | 20.9 | EEEE | 00:00:30.3 |
| 17 | 813.60 | 30.00 | 24.6 | 488.16 | 60.00 | 20.9 | EEEE | 00:00:30.3 |
| 18 | 947.55 | 20.00 | 19.1 | 379.02 | 40.00 | 20.9 | EEEE | 00:00:30.2 |
| 19 | 1270.02 | 10.00 | 12.8 | 254.00 | 20.00 | 20.9 | EEEE | 00:00:30.3 |

TABLE 3

Third run for 21 C. sample.

| # | Viscosity (cP) | Speed (RPM) | % Torque (%) | Shear Stress (D/cm$^2$) | Shear Rate (1/sec) | Temperature (° C.) | Bath (° C.) | Time Interval (mm:ss.t) |
|---|---|---|---|---|---|---|---|---|
| 1 | 4742.72 | 10.00 | 47.8 | 948.54 | 20.00 | 20.9 | EEEE | 00:00:30.8 |
| 2 | 2435.85 | 20.00 | 49.1 | 974.34 | 40.00 | 20.9 | EEEE | 00:00:30.2 |
| 3 | 1696.66 | 30.0 | 51.3 | 1018.00 | 60.00 | 20.9 | EEEE | 00:00:30.3 |
| 4 | 1319.63 | 40.00 | 53.2 | 1055.70 | 80.00 | 20.9 | EEEE | 00:00:30.3 |
| 5 | 1105.31 | 50.00 | 55.7 | 1105.31 | 100.00 | 20.9 | EEEE | 00:00:30.2 |
| 6 | 952.51 | 60.00 | 57.6 | 1143.61 | 120.00 | 20.9 | EEEE | 00:00:30.2 |
| 7 | 840.54 | 70.00 | 59.3 | 1176.75 | 140.00 | 20.9 | EEEE | 00:00:30.3 |
| 8 | 760.27 | 80.00 | 61.3 | 1216.44 | 160.00 | 20.9 | EEEE | 00:00:30.2 |
| 9 | 692.34 | 90.00 | 62.8 | 1246.20 | 180.00 | 20.9 | EEEE | 00:00:30.3 |
| 10 | 638.98 | 100.00 | 64.4 | 1277.95 | 200.00 | 20.9 | EEEE | 00:00:30.3 |
| 11 | 637.21 | 90.00 | 57.8 | 1146.98 | 180.00 | 20.9 | EEEE | 00:00:30.2 |
| 12 | 635.01 | 80.00 | 51.2 | 1016.01 | 160.00 | 20.9 | EEEE | 00:00:30.3 |
| 13 | 642.10 | 70.00 | 45.3 | 898.93 | 140.00 | 20.9 | EEEE | 00:00:30.2 |
| 14 | 653.20 | 60.00 | 39.5 | 783.84 | 120.00 | 20.9 | EEEE | 00:00:30.2 |
| 15 | 672.71 | 50.00 | 33.9 | 672.71 | 100.00 | 20.9 | EEEE | 00:00:30.3 |
| 16 | 714.38 | 40.00 | 28.8 | 571.51 | 80.00 | 20.9 | EEEE | 00:00:30.2 |
| 17 | 793.76 | 30.00 | 24.0 | 476.26 | 60.00 | 20.9 | EEEE | 00:00:30.3 |
| 18 | 873.14 | 20.00 | 17.6 | 349.25 | 40.00 | 20.9 | EEEE | 00:00:30.2 |
| 19 | 1190.64 | 10.00 | 12.0 | 238.13 | 20.00 | 20.9 | EEEE | 00:00:30.3 |

TABLE 4

First run for 37 C. sample.

| # | Viscosity (cP) | Speed (RPM) | % Torque (%) | Shear Stress (D/cm²) | Shear Rate (1/sec) | Temperature (° C.) | Bath (° C.) | Time Interval (mm:ss.t) |
|---|---|---|---|---|---|---|---|---|
| 1 | 677.86 | 5.00 | 27.6 | 67.79 | 10.00 | 36.8 | EEEE | 00:01:01.7 |
| 2 | 528.04 | 10.00 | 43.0 | 105.61 | 20.00 | 36.8 | EEEE | 00:00:30.2 |
| 3 | 459.27 | 15.00 | 56.1 | 137.78 | 30.00 | 36.8 | EEEE | 00:00:30.2 |
| 4 | 408.31 | 20.00 | 66.5 | 163.32 | 40.00 | 36.8 | EEEE | 00:00:30.3 |
| 5 | 371.35 | 25.00 | 75.6 | 185.67 | 50.00 | 36.8 | EEEE | 00:00:30.3 |
| 6 | 375.77 | 20.00 | 61.2 | 150.31 | 40.00 | 36.8 | EEEE | 00:00:30.2 |
| 7 | 386.41 | 15.00 | 47.2 | 115.92 | 30.00 | 36.8 | EEEE | 00:00:30.2 |
| 8 | 416.29 | 10.00 | 33.9 | 83.26 | 20.00 | 36.8 | EEEE | 00:00:30.3 |
| 9 | 483.83 | 5.00 | 19.7 | 48.38 | 10.00 | 36.8 | EEEE | 00:01:00.2 |

TABLE 5

Second run for 37 C. sample.

| # | Viscosity (cP) | Speed (RPM) | % Torque (%) | Shear Stress (D/cm²) | Shear Rate (1/sec) | Temperature (° C.) | Bath (° C.) | Time Interval (mm:ss.t) |
|---|---|---|---|---|---|---|---|---|
| 1 | 741.71 | 5.00 | 30.2 | 74.17 | 10.00 | 36.8 | EEEE | 00:01:01.0 |
| 2 | 545.23 | 10.00 | 44.4 | 109.05 | 20.00 | 36.8 | EEEE | 00:00:30.2 |
| 3 | 442.08 | 15.00 | 54.0 | 132.62 | 30.00 | 36.8 | EEEE | 00:00:30.2 |
| 4 | 395.42 | 20.00 | 64.4 | 158.17 | 40.00 | 36.8 | EEEE | 00:00:30.2 |
| 5 | 352.68 | 25.00 | 71.8 | 176.34 | 50.00 | 36.8 | EEEE | 00:00:30.3 |
| 6 | 353.05 | 20.00 | 57.5 | 141.22 | 40.00 | 36.8 | EEEE | 00:00:30.2 |
| 7 | 369.22 | 15.00 | 45.1 | 110.77 | 30.00 | 36.8 | EEEE | 00:00:30.3 |
| 8 | 390.50 | 10.00 | 31.8 | 78.10 | 20.00 | 36.8 | EEEE | 00:00:30.3 |
| 9 | 478.92 | 5.00 | 19.5 | 47.89 | 10.00 | 36.8 | EEEE | 00:01:00.2 |

Features of the disclosed embodiments may be combined, rearranged, omitted, etc., within the scope of the invention to produce additional embodiments. Furthermore, certain features may sometimes be used to advantage without a corresponding use of other features. It is, thus, apparent that there is provided, in accordance with the present disclosure, a vaginal lubricant. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A vaginal lubricant comprising: 10% jojoba oil, 77.88% sunflower oil, 11% beeswax, 1% cocoa butter, 0.01% shea butter, 0.001% evening primrose oil, 0.01% aloe, 0.001% borage oil, 0.1% flax seed oil, 0.00001% extract blend of arnica and comfrey and 0.00001% coconut oil, wherein the vaginal lubricant has a viscosity below 2000 cP at a shear rate of 100 inverse seconds at a temperature of at least 21° C.

* * * * *